(12) United States Patent
Chun et al.

(10) Patent No.: US 8,965,824 B2
(45) Date of Patent: Feb. 24, 2015

(54) ELECTRONIC PERSONAL ADVOCATE

(71) Applicant: Intel Corporation, Santa Clara, CA (US)

(72) Inventors: Anthony L. Chun, Los Altos, CA (US);
Glen J. Anderson, Beaverton, OR (US);
Albert Yosher, Haifa (IL)

(73) Assignee: Intel Corporation, Santa Clara, CA (US)

( * ) Notice: Subject to any disclaimer, the term of this patent is extended or adjusted under 35 U.S.C. 154(b) by 188 days.

(21) Appl. No.: 13/631,916

(22) Filed: Sep. 29, 2012

(65) Prior Publication Data

US 2014/0095420 A1 Apr. 3, 2014

(51) Int. Cl.
*G06N 5/02* (2006.01)
*G06Q 10/00* (2012.01)

(52) U.S. Cl.
USPC .................................................. 706/46; 705/2

(58) Field of Classification Search
None
See application file for complete search history.

(56) References Cited

U.S. PATENT DOCUMENTS

| | | | |
|---|---|---|---|
| 7,447,643 B1 * | 11/2008 | Olson et al. ........................ | 705/2 |
| 2005/0086082 A1 * | 4/2005 | Braunstein et al. ................ | 705/2 |
| 2008/0218307 A1 | 9/2008 | Schoettle | |
| 2012/0095352 A1 * | 4/2012 | Tran ............................. | 600/490 |

FOREIGN PATENT DOCUMENTS

| | | |
|---|---|---|
| JP | 2000-172394 | 6/2000 |
| WO | 2011-059761 | 5/2011 |
| WO | 2012-110907 | 8/2012 |

OTHER PUBLICATIONS

International Search Report and Written Opinion, mail date Oct. 17, 2013, PCT/ISA/210, PCT/ISA/220, and PCT/ISA/237, total of 10 pages.

* cited by examiner

*Primary Examiner* — Alan Chen
(74) *Attorney, Agent, or Firm* — Pillsbury Winthrop Shaw Pittman LLP

(57) ABSTRACT

According to various aspects of the present disclosure, a system and associated method and functions to anticipate a need of a user are disclosed. In some embodiments, the disclosed system includes a data acquisition unit, a prediction unit, and an operation unit. The data acquisition unit is configured to detect user information, the user information including physiological and non-physiological data associated with the user. The prediction unit is operatively connected to the data acquisition unit to receive the user information, and is configured to anticipate a user need (e.g., need for medical assistance, need for language translation support, etc.) based on pre-defined user preferences, as well as on the physiological data or the non-physiological data or both. And, the operation unit is configured to automatically perform an operation, without user input, to address the user need (e.g., contact a medical facility, provide a language translation application to the user, etc.).

22 Claims, 2 Drawing Sheets

ELECTRONIC PERSONAL ADVOCATE

FIELD OF THE INVENTION

The present invention relates generally to techniques and systems to anticipate needs of a user, and more particularly, to techniques and systems to anticipate a user's needs based on user-related information and perform one or more operations to address the anticipated needs.

BACKGROUND

Typically, electronic assistant devices or applications supporting a user are passive in nature. For example, traditional electronic personal assistant devices or applications may be capable of providing information to the user per configurations or data provided by the user, e.g., reminding the user of events that he/she has programmed into the device. However, such electronic assistant devices or applications do not predict or anticipate and communicate needs of user in order to improve user's well-being or facilitate routine user activities, e.g., by utilizing pre-defined user's preferences and monitored user's physiological information and/or non-physiological information (including location, environmental conditions, etc.).

DETAILED DESCRIPTION

Figure 1:
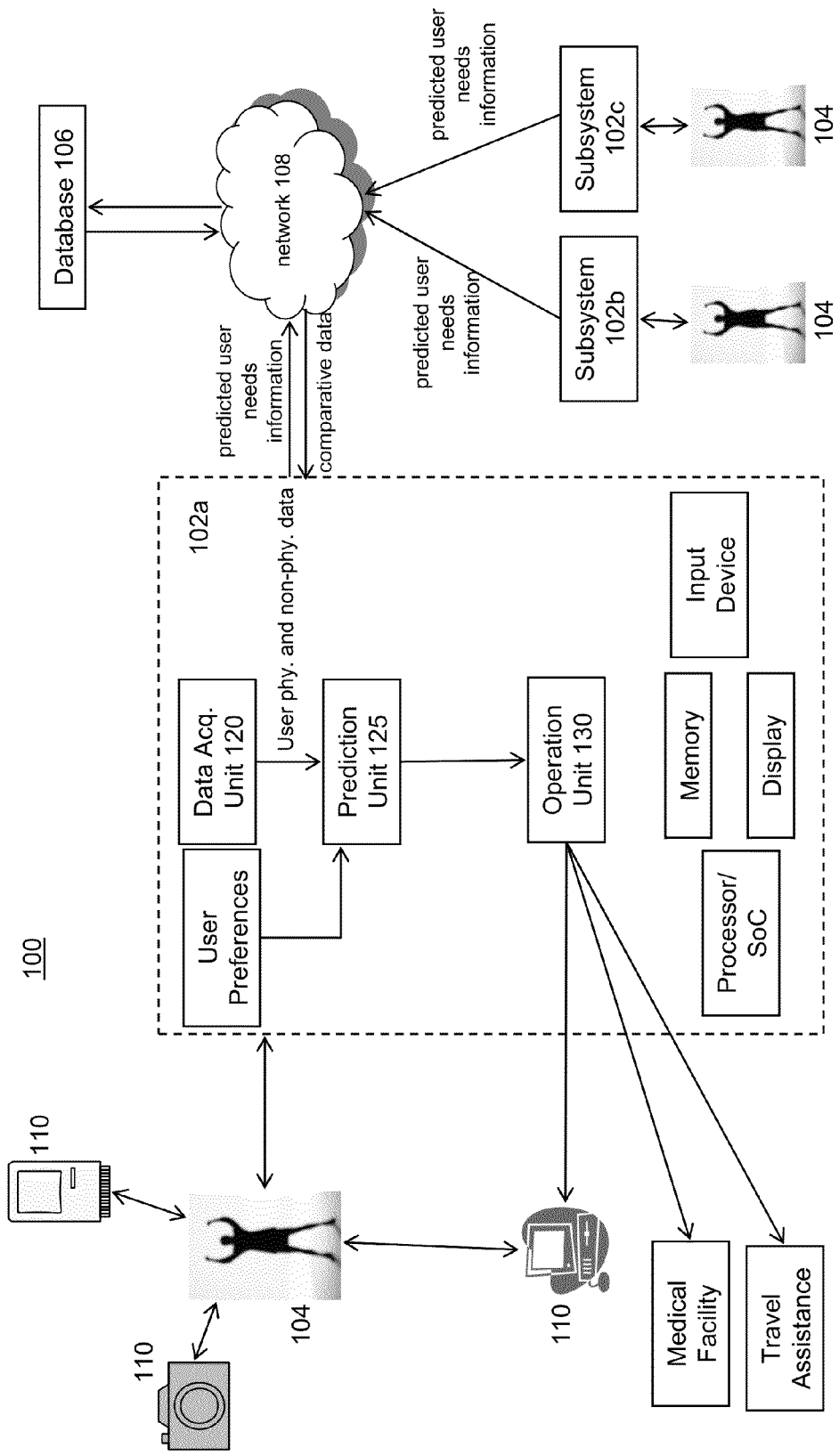
FIG. 1 is a block diagram of a system to anticipate and address needs of a user, in accordance with various embodiments of the present disclosure.

In broad overview, the system and method for anticipating (or predicting) and addressing possible needs of a user in accordance with various embodiments of the present disclosure may be implemented as software, hardware and/or firmware in connection with (or as part of) a computing and/or communication device associated with the user. By way of illustration, such computing device may be a mobile phone, a tablet computer, a personal computer, a server, a laptop, a smartphone, a gaming device, a networking device, or a wearable computing device in the form of a wrist watch, a bracelet, a pair of headphones, a pair of eyeglasses and/or other wearable computing devices. In some embodiments, the disclosed system or method is completely or partially implemented by one or more processing units implanted within the user. Along these lines, the disclosed embodiments may be implemented in association with, or as part of, one or more computing and communication devices of various form factors.

In accordance with various aspects of the present disclosure, a system to anticipate and address a user need is presented. The system may include a data acquisition unit, a prediction unit, and an operation unit. The data acquisition unit may be configured to detect user information including physiological and non-physiological data associated with the user. The non-physiological data may include location of the user, ambient environment conditions, e.g., temperature, internet browsing history of the user, a status of user's stock portfolio, and/or other information not related with the body or biological features of the user. The data acquisition unit may include at least one of a camera, a microphone, an accelerometer, a gyroscope, a location sensor, a temperature sensor to detect ambient temperature, a gesture recognition sensor, and a sensor to detect a physiological parameter of the user.

In some embodiments, the prediction unit operatively connected to the data acquisition unit to receive the user information, and configured to anticipate a user need based on a pre-defined user preference, and the physiological data or the non-physiological data or both. The prediction unit may utilize a pattern recognition or machine learning algorithm to predict the user need. The pre-defined user preference may include a specific user location or a specific time period based on which the prediction unit processes the user information.

Further, the operation unit may be configured to automatically perform an operation to address the anticipated user need without user input, e.g., based on a predetermined preference including a specific user location or a specific time period. The operations may include communicating the predicted user need to the user and/or associated entities (e.g., family or friends), notifying a medical facility or professional (if the predicted need is medical assistance), contacting a local transport service provider (if the predicted need is travel assistance), etc.

In accordance with various embodiments of the present disclosure, a method to anticipate and address a user need is presented. The method may include detecting user information including physiological and non-physiological data associated with the user. Further, the method may include processing the user information and a pre-defined user preference to anticipate a user need based on a pre-defined user preference, and the physiological data or the non-physiological data or both, and automatically performing an operation to address the anticipated user need without user input.

The non-physiological data may include location of the user, ambient environment conditions, e.g., temperature, internet browsing history of the user, a status of user's stock portfolio, performance of user's preferred sports team or candidate in an election, and/or other information not related with the body or biological features of the user. In some embodiments, the operation of detecting user information is performed using at least one of a camera, a microphone, an accelerometer, a gyroscope, a location sensor, a temperature sensor to detect ambient temperature, a gesture recognition sensor, and a sensor to detect a physiological parameter of the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Turning now to the various aspects of the disclosure, FIG. 1 depicts a non-limiting example of a system, i.e., a system 100, in which techniques for anticipating and addressing needs of a user described herein are implemented. As shown, system 100 may include a personal advocate subsystem 102 associated with a user 104, and a prediction database 106 which may be operatively connected with subsystem 102 via one or more networks 108. Alternatively, subsystem 102 may be connected with database 106 directly. Although only one subsystem 102, one user 104, and one database 106 are shown in FIG. 1, system 100 is not limited to that specific configuration. Indeed, there may be multiple users 104 in the system each of which may be associated with (and utilize) their respective personal advocate subsystem 102 such that there is one-to-one correspondence with each subsystem 102 and user 104. Alternatively, two or more users 104 may be associated with one or more subsystems 102. As discussed in detail below, each subsystem 102 may be configured to anticipate and address one or more needs of user 104, and generally, such needs may include medical assistance, travel assistance, safety assistance, and/or other user needs.

Referring now to an example of a detail structure of personal advocate subsystem 102, in some embodiments, subsystem 102 includes a data acquisition unit 120, a prediction unit 125, and an operation unit 130. In some embodiments, data acquisition unit 120 is configured to detect, acquire and/or process user information including physiological and non-physiological data associated with user 104. In the context of this disclosure, user's physiological data include data, information or signals obtained from the user's body and that are related to biological functions and activities (including physical and chemical processes) of the user's body and its parts. For example, user's physiological data may include heart rate, skin and body temperature, blood pressure, blood oxygen level, respiratory rate, posture and motion of user's body or part thereof, user's voice, and/or other known physiological information.

Accordingly, in some embodiments, data acquisition unit 120 is communicatively associated with and/or includes one or more biomedical or health sensors for detecting or sensing signals related to user's physiology. For example, one or more sensors to detect user's heart rate, skin and body temperature, blood pressure, blood oxygen level, and/or respiratory rate, and/or an accelerometer and a gyroscope to determine user's movement and posture may be attached on or implanted within the user's body, and may be configured to acquire and communicate the physiological signals to data acquisition unit 120, e.g., through a wired or wireless connection. Such sensors may be embodied in various different form factors, such as in the form of a wrist watch, a finger ring, a patch directly attached to a part of user's body, a garment worn by the user, and/or other known form factors for such sensors. Additionally, or alternatively, sensors may be part of the environment where the user resides or interacts, e.g., a thermal sensor installed in the user's house to measure body heat or a camera (and associated processing capabilities) to monitor a person's gait.

Further, in the context of this disclosure, non-physiological data for user 104 may include location of the user, ambient conditions of the user, internet browsing history of the user, a status of user's stock portfolio, performance of user's preferred sports team or candidate in an election, and/or other information not related with the body or biological features and functions of user 104. As such, data acquisition unit 120 may be communicatively associated with and/or include a location sensor (e.g., a geographical positioning system (GPS)) to determine the location of user 104, one or more sensors to detect temperature, sound level, or level of brightness/darkness of the environment where user 104 is located, a unit that receives and stores user's internet browsing history from one or more user's client devices or from a server accessed by the server and/or other information related to conditions and characteristics of user's activities. Additionally, or alternatively, data acquisition unit 120 may be communicatively associated with and/or include a photo/video camera (facing the user), a microphone and one or more sensors to detect user's gestures. In some embodiments, data acquisition unit 120 includes a memory storage unit and a processor to store and process various received or acquired sensor data, i.e., user information data. For example, using its processing unit, data acquisition unit 120 may be able to process the photo or video information of user 104 to perform facial recognition, and process user's speech detected by the microphone to perform speech recognition. The facial recognition (or facial expression recognition or face detection) may be performed by data acquisition unit 120 based on one or more algorithms including, for example, SHORE™—Sophisticated High-speed Object Recognition Engine (from Fraunhofer Institute for Integrated Circuits) that does recognition of the presence of faces, as well as the recognition of facial expressions ("happy", "surprised", "angry," and "sad"). In general, the facial recognition techniques are based on geometric techniques which include reviewing and analyzing distinguishing features and measure between landmarks, and photometric techniques which provide a statistical approach that summarizes images into values to be compared against templates. Further, the speech recognition by data acquisition unit 120 may be based on one or more speech recognition algorithms including Sphinx algorithms developed at Carnegie-Mellon University, and algorithms based on Hidden Markov models.

In some embodiments, data acquisition unit 120 includes one or more additional components or modules to process and transform the initial sensor data/signals obtained at data acquisition unit 120 into user information data (including user's physiological and non-physiological data) that is used by prediction unit 125. For example, data acquisition unit 120 may include modules (not shown) that are capable of amplifying, filtering, multiplexing, digitizing, reducing or eliminating noise, converting digital signals into RF signals, and/or other processing specific to the type of physiological/non-physiological signal to generate the user information data for prediction unit 125.

In some embodiments, prediction unit 125 receives the user information from data acquisition unit 120 and information including pre-defined user preferences, e.g., from a memory or storage unit within or associated with subsystem 102. Further, prediction unit 125 is configured to analyze and process the user information and pre-defined user preference data, and based on the analyzed data, anticipate or predict what the user needs to improve user's well-being or facilitate routine activities performed by the user. In some embodiments, a pre-defined user preference includes one or more specific geographical locations, one or more specific events, and one or more specific time periods, which, in general, indicate a trigger for prediction unit 125 to begin processing the user information to determine a possible user need.

In some embodiments, prediction unit 125 uses a supervised (or predictive) machine learning algorithm to predict what kind of assistance user 104 may need. Accordingly, as part of supervised learning algorithm, unit 125 relies on a "training set or sample" of user information for which the target property or classification (i.e., a possible user need) is known with confidence. The training set may include a set of specific values of physiological and non-physiological user data as well as user preferences. Accordingly, each known or classified user need may be associated with user information including a set of specific values of physiological/non-physiological data and user preferences, which are used as standard user information for that particular user need. In some embodiments, the standard user information for a classified user need is obtained by exposing a user or a group of users (like users 104) to one or more controlled environments, e.g., including preselected activities or interactions with preselected ambient conditions, and monitoring user's physiological responses and non-physiological conditions for such controlled environments. In general, the controlled environments cover a parameter space (related to physiological and non-physiological data) for which the supervised machine learning algorithm is used by prediction unit 125. Accordingly, the supervised learning technique is trained on this set of controlled user information, and the resulting mapping is applied to further monitored user information (e.g., obtained using data acquisition unit 120) for which a predicted user requirement is yet to be obtained.

Before prediction unit 125 uses the machine learning algorithm on data received from data acquisition unit 120, prediction unit 125 may preprocess the received data to make it meaningful, and then transform the data in some way as appropriate to the machine learning algorithm. For example, a machine learning algorithm may require "attributes" of the user information, i.e., the values in the data fields describing the properties of each physiological parameter/non-physiological parameter in the user information and of each pre-defined user preference, to be numerical or categorical. It is possible to transform numerical data to categorical and vice versa. A common categorical-to-numerical method is scalarization, in which different possible categorical attributes are given different numerical labels, for example, "fast heart rate," "high skin temperature," and "fast speed" may be labeled as the vectors [1, 0, 0], [0, 1, 0], and [0, 0, 1], respectively. Further, numerical data can be made categorical by transformations such as binning. The bins may be user-specified, or can be generated optimally from the data. Binning can create numerical issues, including comparing two floating point numbers that should be identical, objects on a bin edge, empty bins, values that cannot be binned such as NaN, or values not within the bin range.

In general, the user preference data and the user information from data acquisition unit 120 may include a large number of attributes for each physiological parameter and non-physiological parameter, and not all may be required for determining/predicting a user need. Indeed, use of all attributes may, in some cases, worsen performance. The large number of attributes results in a high-dimensional space with many low density environments or even empty voids. This makes it difficult to generalize from the data and produce useful new results. Therefore, some form of dimension reduction may be employed (by prediction unit 125), in which as much of the information as possible is retained, but in fewer attributes. One example of well-known technique to reduce the dimension of the data is principal component analysis (PCA). PCA is limited to linear relations, and produces, as the principal components, the eigenvectors of the input data, i.e., it picks out the directions or attributes which contain the greatest amount of information. The details of the PCA technique are described in "*Principal Component Analysis*," I. T. Jolliffe, Springer Series in Statistics, $2^{nd}$ Edition. Another dimension reduction approach is forward selection, in which one attribute is selected, and selectively new attributes are considered to gain the most information. Or, backward elimination approach may be used, in which all of the attributes are initially selected, and are selectively removed to reduce the number of attributes but maintaining maximum information.

After obtaining appropriate attributes of user preferences and physiological and non-physiological parameters of the user information, and based on the training set, prediction unit 125 may use a supervised machine learning algorithm, e.g., support vector machine (SVM) technique to predict a need or requirement of user 104. In general, SVM aims to find the hyper-plane that best separates two or more classes of data. The input data, i.e., the user information data, are viewed as sets of vectors and the data points closest to the classification boundary are the support vectors. In general, the input user data is arranged in a multidimensional space, for example, in a vector of numerical values comprised of numerical representations of different measured parameters, e.g., for "measured speech stress state," "facial feature state," "measured heart rate," "measured blood pressure," etc. The SVM algorithm creates the decision boundaries in the multi-dimensional space (using a hyper-plane), which are defined in terms of the support vectors, and different divided spaces correspond to different user needs, e.g., "medical emergency assistance," "language translation assistance," "safety assistance," etc. The input attributes are mapped into a higher-dimensional space using a kernel so that nonlinear relationships within the data become linear, and the decision boundaries, which are linear, are determined in this space. The SVM algorithm minimizes a cost function, which in this case is the number of incorrect classifications. The algorithm has two adjustable hyper-parameters: the width of the kernel, and the regularization, or cost, of classification error, which helps to prevent overfitting of the training set. The shape of the kernel is also an adjustable parameter, a common choice being the Gaussian radial basis function. SVM is generally designed to classify objects into two classes. However, various refinements may be made to the SVM algorithm to support additional classes, and to perform regression, i.e., to supply a continuous output value instead of a classification. Classification probabilities can be output, for example, by using the distance of a data point from the decision boundary. The details of the SVM algorithm can be found in "*The Nature of Statistical Learning Theory*," V. Vapnik, 2nd Edition (Springer, New York, 1999), "*An Introduction to Support Vector Machines and Other Kernel-based Learning Methods*," N. Cristianini and J. Shawe-Taylor, (Cambridge University Press, 2000), and "*Learning and Soft Computing: Support Vector Machines, Neural Networks, and Fuzzy Logic Models*," V. Kecman (MIT Press, Cambridge, Mass., 2001).

In some embodiments, prediction unit 125 is configured to use other supervised machine learning algorithms, such as, but not limited to, artificial neural network technique, decision tree algorithm, and k nearest neighbor method. Further, prediction unit 125 is configured to use unsupervised methods such as, but not limited to, kernel density estimation method, K-means clustering method, and expectation maximization method.

In operation, for example, user information from data acquisition unit 120 may include data indicating that user 104 is under stress (based on information from one or more health sensors on the user's body). Based on such information and a pre-defined user preference of preferred medical facility or professional, prediction unit 125, using, e.g., the SVM technique, may predict or anticipate that user 104 needs medical assistance, e.g., from the preferred medical facility or professional. In this case, prediction unit 125 may also be able to determine what a particular medical issue which user 104 may be experiencing and as such, predict a specific type of medical assistance that user 104 needs.

In another example, user information from data acquisition unit 120 may include data indicating that user 104 is presently located in a foreign country (based on GPS data), e.g., where the spoken and written language is different than the language (s) known or used by user 104 (as indicated in user preferences). In this example, based on user's location information and user language preferences, prediction unit 125 may predict or anticipate that user 104 needs to have local language and gesture capabilities on his/her device (e.g., a smartphone). Additionally, or alternatively, prediction unit 125 may also anticipate that user 104 would need local transportation options, hotel/restaurant reservations, real-time speech translation support, etc., in the foreign country.

In yet another example, user information from data acquisition unit 120 may include data indicating that user 104 is presently located in unsafe neighborhood (based on GPS data), is being approached by strangers with threatening gestures (based on gesture recognition and video sensors), is asking for help (based on speech recognition), and have an elevated heart rate (based on a health sensor). Based on such information, prediction unit 125 may predict or anticipate that user 104 needs safety assistance, e.g., from local police or other public safety authorities.

In a further example, user information from data acquisition unit 120 may include user 104's present location (based on GPS data), and user's appointment at a specific destination location as extracted from a "calendar application," e.g., which is executing on the user's phone or tablet computer. Based on such information, prediction unit 125 may predict or anticipate user 104 needs an indication of an estimated time when the user should from the present location to reach the destination location on time for the appointment.

In another example, user information may include user preferences when in a flight, e.g., "would not like to be disturbed when asleep," or "would like to have a meal," and, from data acquisition unit 120, may include information that user is currently sleeping and video data that a flight attendant is making rounds with the food cart. Based on such information, prediction unit 125 may predict that there is a need to communicate user's flight preference to the flight attendant so that the flight attendant acts accordingly.

In some embodiments, prediction unit 125 is in communication with database 106, which may store outputs from outputs and associated user information from unit 125 of subsystem 102 as well as from similar units 125 of other subsystems 102. Database 106 may include appropriate software and hardware to process such collective information to generate comparative data related to predicted user needs and corresponding user information and preferences. Accordingly, in some embodiments, prediction unit 125 may send user information provided by unit 120 and user preference information to database 106, and request and utilize comparison data from database 106 that indicate predicted user need(s) for other user(s) who had similar physiological/non-physiological conditions and similar user preferences. As such, in addition to information from unit 120 and preference information for user 104, unit 125 may also include the comparison data from database 106 to determine an anticipated need for user 104.

In operation, prediction unit 125 may convey the predicted or anticipated user need(s) to operation unit 130. In some embodiments, operation unit 130 communicates or reports the predicted user need to user 104 and/or associated entities (e.g., family or friends of user 104). For example, operation unit 130 may communicate the anticipated need(s) as determined by unit 125 to device(s) 110 associated with or operated by user 104, such that an user 104 and/or associated entities are notified of the user's anticipated need(s). A communication from operation unit 130 to device(s) 110 may be in the form of text message, e-mail message, voice message, an image, etc., or in the form of message broadcasted through a social media application (e.g., Facebook, etc.). Devices 110 may be a computing and/or a communication device capable of connecting to one or more networks, such as, the Internet, a cellular network, a wired network, etc. Such devices may include a mobile phone, a smartphone, a tablet computer, a personal computer, a laptop, a smartphone, a gaming device, or a wearable device in the form of a wrist watch, a bracelet, a pair of headphones, a pair of eyeglasses and/or other wearable/implantable computing devices. Additionally, or alternatively, devices 110 may include a display device, such as a TV, public glass display, automobile display, etc. Devices 110 may also tactile (haptic), or text-to-speech capability of communicating information and reminders to the user.

In addition to communicating the user's anticipated need (as determined by prediction unit 125), operation unit 130 is also configured to automatically perform one or more operations to address the anticipated user need(s) without user input. For example, in the above example where prediction unit 125 predicts that user 104 needs medical assistance, operation unit 130 may automatically initiate a call to user's preferred or nearest or an available medical facility and/or professional through a phone device 110, and send the biomedical sensor data (from data acquisition unit 120), e.g., in an email message or through some other communication means to the medical facility and/or professional. As an additional operation, operation unit 130 may also acquire user's medical history reports (e.g., from a healthcare database) and send them to the medical facility and/or professional. Further, to ensure that device 110 is in constant communication with the medical facility and/or professional, operation unit 130 may also alter communication settings of device 110. For example, if device 110 is a smartphone capable of operating using multiple wireless technologies, but and is currently only operational on one technology (e.g., Wi-Fi), operation unit 130 may automatically alter the device's communication settings to activate an additional technology (e.g., cellular 3G/4G) on the device. Moreover, based on the urgency of the predicted medical issue, operation unit 130 may notify the medical facility/professional over multiple communication mechanisms and wireless capabilities (e.g., using both the WiFi network and cellular network) to ensure timely delivery of the emergency notification, or automatically choose one wireless technology if another is detected to be non-functional on device 110. In addition, operation unit 130 may monitor the user's medication schedule and dosage and remind the user when to take his/her medication. Operation unit 130 may be configured to recognize that the user has taken his/her medicine through image analysis, and sends an alarm if the medication is not taken.

Similarly, in the above example where prediction unit 125 anticipates that user 104 needs to have local language and gesture capabilities on his/her device 110 (e.g., a smartphone), operation unit 130 may automatically reconfigure device's language capabilities such that some information on the device is presented to the user in the local language, or initiate a download and installation of an application which provides real-time language translation to the local language and appropriate local gesture information on the user device. Operation unit 130 may also be configured to communicate to local services to arrange for transportation to a specific destination (e.g., a hotel) for user 104, and communicate to a restaurant a request for reservation for user 104 and present the menu to the user in user's preferred language.

Further, in the above example where prediction unit 125 predicts that user 104 needs safety assistance, operation unit 130 may initiate a call through phone 110 to local authorities (e.g., by using the "911" service), or initiate computation of a fastest route on GPS device 110 to drive out of the unsafe neighborhood.

Similarly, in the above example where prediction unit 125 predicts that user 104 needs an indication of an estimated time when the user should from the present location to reach the destination location on time for the appointment, operation unit 130 may automatically acquire current traffic conditions for the route from the user's current location to the destination location, compute estimated travel time, and based on that, present on device 110 a suggestion message (e.g., in the form of a text) including estimated starting time for user 104.

Further, in the above example where prediction unit 125 anticipates that there is a need to communicate user's flight preference to the flight attendant, operation unit 130 may communicate a status message indicating user's preference ("would not like to be disturbed when asleep," or "would like to have a meal,") to a device carried or operated by the flight attendant.

In some embodiments, after an action or function is performed to address the predicted user need, operation unit 130 send a query message to user 104 (e.g., at user device 110) to confirm whether the prediction from prediction unit 125 (and the action thereafter) was accurate, confirm whether (and which) additional actions need to be taken, or request user 104 to provide further detailed preferences to personal advocate subsystem 102 to improve the prediction process and/or adjust the operation(s) performed thereafter.

In other embodiments, operation unit 130 transmits the predicted need message and/or performs the required operation in accordance with a predetermined preference. The predetermined preference may be preselected by the user, and stored in a memory accessible by the operation unit. The predetermined reporting preferences may include one or more specific geographical locations, one or more specific events, and one or more specific time periods, which, in general, indicate a trigger for operation unit 130 to begin communicating the predicted user need to device(s) 110, or execute the operation(s) to fulfill the anticipated user need(s).

In some embodiments, subsystem 102 (or units thereof) is embodied in an electronic, computing and communication device of one of various form factors. Such device may be a mobile phone, a tablet computer, a personal computer, a server, a laptop, a smartphone, a gaming device, a networking device, or a wearable computing device in the form of a wrist watch, a bracelet, a pair of headphones, a pair of eyeglasses and/or other wearable computing devices. In some embodiments, subsystem 102 (or units thereof) is completely or partially implemented by one or more processing units implanted within user 104. Subsystem 102 (or units thereof) may be part of device 110.

In some embodiments, device implementing subsystem 102 includes a display device, input devices, a memory, a system-on-chip (SoC) chipset, a communication module, and an antenna. The device may also include a bus and/or other interconnection means to connect and communicate information between various components or units of the device.

The display device may be configured to display information to a user and may comprise a liquid crystal display (LCD), a light emitting diode (LED)-based display, or any other flat panel display, or may use a cathode ray tube (CRT). The input devices may include alphanumeric and other keys which may be inputted via a keyboard, touch screen (e.g., with haptics or tactile feedback), speech input, eye tracking input, gesture input, brain monitoring systems or other comparable input mechanism. The input information received through one or more of the input devices may be communicated to a processor of the SoC, e.g., via a bus, for further processing. Another type of the input device may include a cursor control device, such as a mouse, a trackball, or cursor direction keys to communicate direction information and command selections, e.g., to the SoC and to control cursor movement on the display device.

The memory of the subsystem device (or any other part of system 100) may be a dynamic storage device configured to store information and instructions to be executed by processors of the SoC and/or other processors (or computing units) in accordance with the embodiments described herein. The memory may also be used to store temporary variables or other intermediate information during execution of instructions by the processors. Some or all of the memory may be implemented as Dual In-line Memory Modules (DIMMs), and may be one or more of the following types of memory: Static random access memory (SRAM), Burst SRAM or SynchBurst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), or any other type of memory device. The device may also include read only memory (ROM) and/or other static storage device configured to store static information and instructions to be executed by processors of the SoC and/or other processors (or computing units) in accordance with the embodiments of this disclosure. Further, the device may include a magnetic disk, optical disc or flash memory devices to store information and instructions to be executed by processors of the SoC and/or other processors (or computing units) in accordance with the embodiments of this disclosure.

In some embodiments, the SoC is part of a core processing or computing unit of the subsystem device, and is configured to receive and process input data and instructions, provide output and/or control other components of subsystem 102 in accordance with embodiments of the present disclosure. The SoC may include a microprocessor, a memory controller, a memory and peripheral components. The microprocessor may further include a cache memory (e.g., SRAM), which along with the memory of the SoC may be part of a memory hierarchy to store instructions and data. The microprocessor may also include one or more logic modules such as a field programmable gate array (FPGA) or other logic array. Communication between the SoC's microprocessor and memory may be facilitated by the memory controller (or chipset), which may also facilitate in communicating with the peripheral components, such as counter-timers, real-time timers and power-on reset generators. The SoC may also include other components including, but not limited to, timing sources (e.g., oscillators and phase-locked loops), voltage regulators, and power management circuits.

In some embodiments, the device implementing is configured to communicate with other devices or systems directly or via one or more networks using a communication module. The communication module may include necessary and typical hardware, software and/or firmware modules, e.g., related to a modulator, a demodulator, a baseband converter, a channel codec, and/or other components, implemented therein to enable the device for wireless communication. As such, the communication module is able to wirelessly transmit and receive data and messages in form of radio frequency (RF) signals through an antenna. In some embodiments, the communication module is designed and configured to support communication based on one or more communication standards and protocols (e.g., to communicate with network 108) including, but not limited to, Wi-Fi, Wi-Gi, Bluetooth, GSM, CDMA, GPRS, 3G or 4G (e.g., WiMAX, LTE) cellular standards, Wireless USB, satellite communication, and Wireless LAN. Additionally, or alternatively, the communication module may also be configured for wired communication, e.g., based on the Ethernet standard, and as such, may be coupled to an appropriate network interface of the device.

Figure 2:
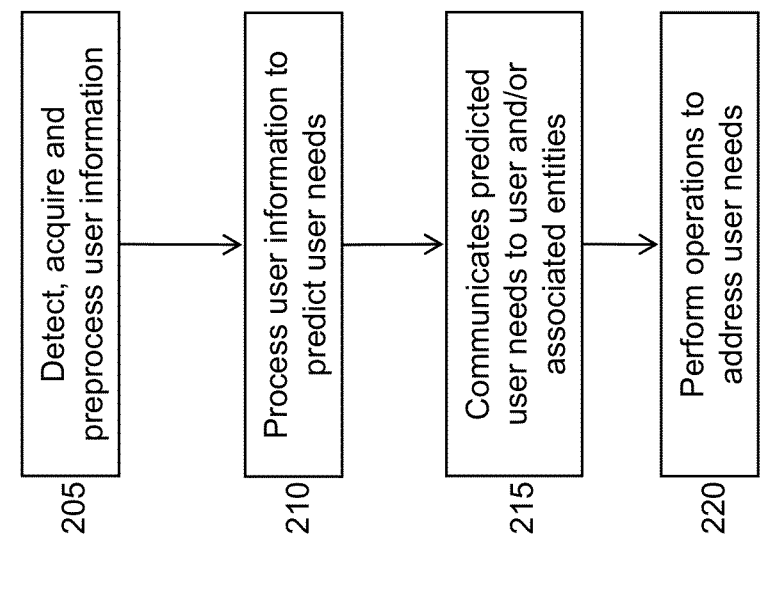
FIG. 2 is a flowchart of a method to anticipate and address needs of a user, in accordance with various embodiments of the present disclosure.

Referring now to FIG. 2 which is flowchart of a method 200 to determine an anticipated need of a user 104 within system 100, e.g., using subsystem 102, in accordance with various embodiments disclosed herein. The anticipated need may improve user's well-being or facilitate routine user activities. For example, method 200 may commence at operation 205 in which data acquisition unit 120 detects, acquires and/or processes user information including physiological and non-physiological data associated with user 104. As discussed above, data acquisition unit 120 detects and obtains user's physiological and non-physiological data via one or more sensors and other devices (e.g., a camera, a microphone, etc.) that are associated with user 104 and/or part of data acquisition unit 120. Data acquisition unit 120 may process and transform the obtained sensor data/signals into user information data (including user's physiological and non-physiological data) that is used by prediction unit 125 further in method 200. For example, data acquisition unit 120 may amplify, filter, multiplex, digitize, reduce or eliminate noise, convert digital signals into RF signals, and/or perform other processing specific to the type of physiological/non-physiological signal to generate the user information data.

Further, in operation 210, the information from unit 120 and user preference information (collectively, "user information") are processed, e.g., by prediction unit 125 to predict what user 104 may need to maintain user's well-being or facilitate user's activities. Prediction unit 125 may also communicate with database 106 to obtain comparative data of other users under similar conditions, as discussed above. Prediction unit 125 may then preprocess and transform the user information (and the received comparative data), and use one or more machine learning techniques (e.g., SVM technique) to process the transformed data to predict the user's need(s) (e.g., need for medical assistance, language assistance, safety assistance, etc.), as discussed above.

In operation 215, operation unit 130 receives the predicted need(s) of user 104 from prediction unit 125, and communicates or reports the predicted user need(s) to user 104 and/or associated entities (e.g., family or friends of user 104). A communication from operation unit 130 to user 104 and/or associated entities operating devices 110 may be in the form of text message, e-mail message, voice message, an image, etc.

In operation 220, operation unit 130 automatically performs one or more operations (without user input) to address the anticipated user need(s). For example, operation unit 130 automatically initiates a call and send user's health data to user's preferred or nearest or an available medical facility and/or professional in the case of anticipated medical assistance; reconfigures device's language and gesture capabilities in the case of anticipated need for local language and gesture capabilities on user device 110; initiates a call through phone 110 to local authorities (e.g., by using the "911" service), or initiates computation of a fastest route on GPS device 110 to drive out of the unsafe neighborhood, in the case of anticipated safety assistance; and/or other operations based on various situations and environment experienced by the user.

Various embodiments herein are described as including a particular feature, structure, or characteristic, but every aspect or embodiment may not necessarily include the particular feature, structure, or characteristic. Further, when a particular feature, structure, or characteristic is described in connection with an embodiment, it will be understood that such feature, structure, or characteristic may be included in connection with other embodiments, whether or not explicitly described. Thus, various changes and modifications may be made to this disclosure without departing from the scope or spirit of the inventive concept described herein. As such, the specification and drawings should be regarded as examples only, and the scope of the inventive concept to be determined solely by the appended claims.

What is claimed is:

1. A system to anticipate a need of a user, the system comprising:
    a data acquisition unit configured to detect user information, the user information including physiological and non-physiological data associated with the user, wherein the non-physiological data comprises location of the user, ambient temperature of the user, and information about internet-based user activity;
    a prediction unit operatively connected to the data acquisition unit to receive the user information, and configured to anticipate a user need based on a pre-defined user preference, and the physiological data or the non-physiological data or both; and
    an operation unit configured to automatically perform an operation to address the anticipated user need without user input.

2. The system of claim 1, wherein the data acquisition unit comprises at least one of a camera, a microphone, an accelerometer, a gyroscope, a location sensor, a temperature sensor to detect ambient temperature, a gesture recognition sensor, and a sensor to detect a physiological parameter of the user.

3. The system of claim 1, wherein the operation unit is configured to automatically perform the operation based on a predetermined preference including a specific user location or a specific time period.

4. The system of claim 1, wherein the pre-defined user preference comprises a specific user location or a specific time period.

5. The system of claim 1, wherein at least one of the data acquisition unit, the prediction unit, and the operation unit is embodied in a mobile phone, a tablet computer or a wearable computing device, or implanted within the user.

6. The system of claim 5, wherein the wearable computing device is a wrist watch, a bracelet, a pair of headphones, or a pair of eyeglasses.

7. The system of claim 1, wherein, based on the user's physiological data, the anticipated user need includes medical assistance to the user, and the operation unit is configured to automatically perform one or more operations including communicating at least part of the user information to a medical facility or personnel, sending a notification message to the user that the medical facility has been contacted, and sending a recommendation message to the user suggesting a specific dosage of a medication to be administered by the user.

8. The system of claim 1, wherein, based on a current geographical location of the user, the anticipated user need includes language translation support and transportation assistance, and the operation unit is configured to automatically perform one or more operations including providing a language translation application to a user device in accordance with a current location of the user, and communicating a reservation of a vehicle for the user to a local transport facility.

9. A method to anticipate a need of a user, the method comprising:

detecting user information, the user information including physiological and non-physiological data associated with the user, wherein the non-physiological data comprises location of the user, ambient temperature of the user, and information about internet-based user activity;

processing the user information and a pre-defined user preference to anticipate a user need based on a pre-defined user preference, and the physiological data or the non-physiological data or both; and automatically performing an operation to address the anticipated user need without user input.

10. The method of claim 9, wherein said detecting comprises detecting the user information using at least one of a camera, a microphone, an accelerometer, a gyroscope, a location sensor, a temperature sensor to detect ambient temperature, a gesture recognition sensor, and a sensor to detect a physiological parameter of the user.

11. The method of claim 9, wherein the pre-defined user preference comprises a specific user location or a specific time period.

12. The method of claim 9, wherein said automatically performing the operation includes automatically performing the operation based on a predetermined preference including a specific user location or a specific time period.

13. The method of claim 9, wherein, based on the user's physiological data, the anticipated user need includes medical assistance to the user, and said automatically performing an operation includes automatically performing one or more of communicating at least part of the user information to a medical facility or personnel, sending a notification message to the user that the medical facility has been contacted, and sending a recommendation message to the user suggesting a specific dosage of a medication to be administered by the user.

14. The method of claim 9, wherein, based on a current geographical location of the user, the anticipated user need includes language translation support and transportation assistance, and said automatically performing an operation includes automatically performing one or more of providing a language translation application to a user device in accordance with a current location of the user, and communicating a reservation of a vehicle for the user to a local transport facility.

15. A non-transitory computer-readable medium comprising computer readable code physically embodied thereon which, when executed by a processor causes the processor to carry out functions comprising:

detecting user information, the user information including physiological and non-physiological data associated with the user, the non-physiological data comprises location of the user, ambient temperature of the user, and information about internet-based user activity;

processing the user information and a pre-defined user preference to anticipate a user need based on a pre-defined user preference, and the physiological data or the non-physiological data or both; and automatically performing an operation to address the anticipated user need without user input.

16. The computer-readable medium of claim 15, wherein said detecting comprises detecting the user information using at least one of a camera, a microphone, an accelerometer, a gyroscope, a location sensor, a temperature sensor to detect ambient temperature, a gesture recognition sensor, and a sensor to detect a physiological parameter of the user.

17. The computer-readable medium of claim 15, wherein the pre-defined user preference comprises a specific user location or a specific time period.

18. The computer-readable medium of claim 15, wherein said automatically performing the operation includes automatically performing the operation based on a predetermined preference including a specific user location or a specific time period.

19. The computer-readable medium of claim 15, wherein, based on the user's physiological data, the anticipated user need includes medical assistance to the user, and said automatically performing an operation includes automatically performing one or more of communicating at least part of the user information to a medical facility or personnel, sending a notification message to the user that the medical facility has been contacted, and sending a recommendation message to the user suggesting a specific dosage of a medication to be administered by the user.

20. The computer-readable medium of claim 15, wherein, based on a current geographical location of the user, the anticipated user need includes language translation support and transportation assistance, and said automatically performing an operation includes automatically performing one or more of providing a language translation application to a user device in accordance with a current location of the user, and communicating a reservation of a vehicle for the user to a local transport facility.

21. The computer-readable medium of claim 15, wherein the processor is embodied in a mobile phone, a tablet computer or a wearable computing device, or implanted within the user.

22. The computer-readable medium of claim 21, wherein the wearable computing device is a wrist watch, a bracelet, a pair of headphones, or a pair of eyeglasses.

* * * * *